(12) United States Patent
Kurachi et al.

(10) Patent No.: US 7,838,452 B2
(45) Date of Patent: Nov. 23, 2010

(54) ULTRAVIOLET RAY TRANSMITTING GLASS COMPOSITION AND GLASS ARTICLE MAKING USE OF THE SAME

(75) Inventors: Junji Kurachi, Tokyo (JP); Koji Fujita, Tokyo (JP); Haruki Niida, Tokyo (JP); Akihiro Koyama, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 523 days.

(21) Appl. No.: 11/887,848

(22) PCT Filed: Apr. 5, 2006

(86) PCT No.: PCT/JP2006/307236
§ 371 (c)(1),
(2), (4) Date: Oct. 4, 2007

(87) PCT Pub. No.: WO2006/107077
PCT Pub. Date: Oct. 12, 2006

(65) Prior Publication Data
US 2009/0075805 A1  Mar. 19, 2009

(30) Foreign Application Priority Data
Apr. 5, 2005 (JP) ............... 2005-108946

(51) Int. Cl.
*C03C 3/083* (2006.01)
*C03C 3/085* (2006.01)
(52) U.S. Cl. .............. 501/68; 501/69; 501/70; 501/71; 501/59
(58) Field of Classification Search .......... 501/59, 501/66, 68, 69, 70, 71
See application file for complete search history.

(56) References Cited

U.S. PATENT DOCUMENTS

| | | | |
|---|---|---|---|
| 1,830,902 A | 11/1931 | Hood | |
| 3,994,708 A | 11/1976 | von Reth et al. | |
| 4,792,535 A | 12/1988 | Fine | |
| 5,204,293 A | 4/1993 | Amundson, Jr. et al. | |
| 5,547,904 A | 8/1996 | Watzke et al. | |
| 6,511,843 B2 * | 1/2003 | Mizuno et al. | ............ 435/287.2 |
| 6,846,760 B2 | 1/2005 | Siebers et al. | |
| 2004/0137444 A1 | 7/2004 | Goto et al. | |
| 2006/0169316 A1 * | 8/2006 | Thomsen et al. | ............ 136/251 |

FOREIGN PATENT DOCUMENTS

| | | | |
|---|---|---|---|
| EP | 1726573 A1 * | 11/2006 | |
| JP | 61-270234 | 11/1986 | |
| JP | 64-79035 | 3/1989 | |
| JP | 2-252636 | 10/1990 | |
| JP | 5-193983 | 8/1993 | |
| JP | 2000-315477 | 11/2000 | |
| JP | 2001-337072 | 12/2001 | |
| JP | 2001-354446 | 12/2001 | |
| JP | 2002-171988 | 6/2002 | |
| JP | 2002338296 A * | 11/2002 | |
| JP | 2007137705 A * | 6/2007 | |
| WO | WO 2005033031 A1 * | 4/2005 | |
| WO | WO 2007058205 A1 * | 5/2007 | |

OTHER PUBLICATIONS

Derwent Abstract 2005-306066, Abstract of WO 2005/033031 A1 and EP 1726573 A1, Apr. 14, 2005.*
Varshneya, A., "Fundamentals of inorganic glasses", Academic Press, Inc. 1994, pp. 214-219.
Sigel, G.H.. "Ultraviolet spectra of silicate glasses: a review of some experimental evidence", Journal of Non-Crystalline Solids, vol. 13, 1973, pp. 372-398.

* cited by examiner

*Primary Examiner*—Karl E Group
*Assistant Examiner*—Elizabeth A Bolden
(74) *Attorney, Agent, or Firm*—Hamre, Schumann, Mueller & Larson, P.C.

(57) ABSTRACT

An ultraviolet ray transmitting glass composition including the following components, in terms of mass % or mass ppm: 60 to 79% $SiO_2$; 0 to 1% $B_2O_3$; exceeded 0% but not more than 20% $Al_2O_3$; 0 to 10% $Li_2O$; 5 to 20% $Na_2O$; 0 to 15% $K_2O$; 0 to 10% MgO; 0 to 10% CaO; 0 to 15% SrO; 0 to 2% refining agent; 2 to 20 ppm $T\text{-}Fe_2O_3$ (in which $T\text{-}Fe_2O_3$ denotes a total iron oxide content obtained by converting all of iron compounds into $Fe_2O_3$); and 0 to 200 ppm $TiO_2$. The ultraviolet ray transmitting glass composition is suitable for a glass article, such as a bioanalytical device that is used for analysis using ultraviolet rays.

18 Claims, 4 Drawing Sheets

US 7,838,452 B2

ULTRAVIOLET RAY TRANSMITTING GLASS COMPOSITION AND GLASS ARTICLE MAKING USE OF THE SAME

TECHNICAL FIELD

The present invention relates to an ultraviolet ray transmitting glass composition, particularly an ultraviolet ray transmitting glass composition that is suitable for a material for bioanalytical devices such as a microplate, and a glass article making use of the same.

BACKGROUND ART

Recently, analysis to be carried out using ultraviolet light has been practiced widely in the field of, for instance, bioanalysis, particularly DNA analysis. A method in which DNA analysis is carried out accurately by determining ultraviolet ray absorption relative to a wavelength of 260 nm is disclosed in JP2002-171988 A.

In such a bioanalysis, an organic solvent such as, for example, isooctane may be used in some cases. Accordingly, materials that are not dissolved in organic solvents are required to be used for the analytical devices.

Conventionally, synthetic resin such as polystyrene generally is used as a material for the above-mentioned analytical devices. Such synthetic resin, however, does not have sufficient resistance to organic solvents. But then, when the resistance to organic solvents is improved, the ultraviolet ray transmittance of the synthetic resin tends to decrease. Accordingly, an inorganic glass composition tends to be used widely as the material for the analytical devices.

Examples of the glass having both a high resistance to organic solvents and a high transmittance for ultraviolet rays, especially ultraviolet rays having a wavelength around the range of 250 to 260 nm, include silica glass. In addition, as the glass having the above-mentioned properties, UV transmitting glass is disclosed in JP 64(1989)-79035 A and glass for a sterilizing lamp is disclosed in JP 2(1990)-252636 A. Additionally, as the glass having a high transmittance for ultraviolet rays having a wavelength around 300 nm, glass for a near-ultraviolet fluorescent lamp is disclosed in JP 61(1986)-270234 A.

The above-mentioned glass having the high ultraviolet ray transmittance, however, has the following problem.

Since the silica glass has a very high glass transition temperature and a very high softening temperature, the forming process of the silica glass by heating and softening is very difficult. Therefore, when the analytical devices described above are made using the silica glass, they are too expensive. In addition, since the silica glass has a considerably lower thermal expansion coefficient, the silica glass cannot be fusion bonded with such as commercial soda-lime silica glass that is available at a low price in producing the analytical devices described above.

The UV transmitting glass disclosed in JP 64(1989)-79035 A includes 15 to 18 wt % boron oxides as an essential component. When a silica glass composition includes alkali metal oxides, the ultraviolet ray transmittance decreases by generation of nonbridging oxygen. When the boron oxide is super-added to the glass composition, the nonbridging oxygen generated binds to the boron and the nonbridging oxygen does not stay in the glass composition. It follows that the glass composition has a high ultraviolet ray transmittance.

However, there is a problem in that boron oxide tends to vaporize from a glass melt. When boron oxide or boron compound vaporizes from a glass melt surface in melting glass, a composition of glass in the vicinity of the glass melt surface may be different from that of glass in the part other than the glass melt surface, and cords may occur in glass articles. Further, the boron oxide or boron compound volatilized erodes material such as a refractory of a melting furnace. When the refractory, etc. are eroded, there is a risk not only that the lifetime of the melting furnace is shortened but also that the ultraviolet ray transmittance of the glass composition deteriorates due to mixing of the eroded refractory into the glass melt.

The glass for a sterilizing lamp described in JP 2(1990)-252636 A includes 11 to 20 wt % of BaO+SrO. Barium is designated as one of type I designated chemical substances in the enforcement ordinance under the law of "Law concerning Reporting, etc. of Releases to the Environment of Specific Chemical Substances and Promoting Improvements in Their Management". Therefore, it is not preferable that the glass composition includes boron oxide from the standpoint in which the trouble on environmental preservation is prevented beforehand. The analytical devices made of glass containing SrO become expensive because SrO is an expansive substance.

The healthy ray fluorescent lamp described in JP 61(1986)-270234 A has a transmittance of about 40% or more relative to a wavelength in the range of 280 to 320 nm. The glass, however, cannot be used as a material for analytical devices that are used with ultraviolet rays having a wavelength in the range of 250 to 260 nm. This is because the glass does not transmit ultraviolet rays having a wavelength in the range of shorter than 270 nm.

DISCLOSURE OF INVENTION

It is an object of the present invention to provide an ultraviolet ray transmitting glass composition and a glass article making use of the same. The glass composition has a high ultraviolet ray transmittance relative to a wavelength in the range of 250 to 260 nm particularly, and a small load on the environment. Furthermore, the glass composition easily can be defoamed and refined at a low cost, and can be joined to common commercial soda-lime silica glass.

The present inventors studied about the relationship between an ultraviolet ray transmittance of a glass composition and the contents of impurities, particularly transition metals, contained in the glass. As a result of the studies, the inventors found out that a glass composition having an ultraviolet ray transmittance the same or higher than that of a glass composition containing boron oxide can be obtained by decreasing the contents of iron oxide and titanium oxide particularly. As a result of further detailed studies, the inventors found out that the number of fine bubbles in the glass articles produced using a glass composition can be decreased considerably by adding the predetermined amount of iron oxide in the glass composition.

An ultraviolet ray transmitting glass composition of the present invention includes the following components, in terms of mass % or mass ppm: 60 to 79% $SiO_2$; 0 to 1% $B_2O_3$; exceeded 0% but not more than 20% $Al_2O_3$; 0 to 10% $Li_2O$; 5 to 20% $Na_2O$; 0 to 15% $K_2O$; 0 to 10% MgO; 0 to 10% CaO; 0 to 15% SrO; 0 to 2% refining agent; 2 to 20 ppm T-$Fe_2O_3$ (in which T-$Fe_2O_3$ denotes a total iron oxide content obtained by converting all of iron compounds into $Fe_2O_3$); and 0 to 200 ppm $TiO_2$. In the present description, the refining agent is a component that has a refining function and is other than the components indicated above.

The ultraviolet ray transmitting glass composition of the present invention makes it possible to provide glass articles having a high ultraviolet ray transmittance relative to a wavelength in the range of 250 to 260 nm and having fewer remaining bubbles easily without increasing the load on the environment. Furthermore, the present invention makes it possible to provide an ultraviolet ray transmitting glass composition having an average linear thermal expansion coefficient (hereinafter, the average linear thermal expansion coefficient may be referred to as an average thermal expansion coefficient or a thermal expansion coefficient) in the range of 50 to 350° C. of 80 to 100×10$^{-7}$/° C. Accordingly, the present invention makes it possible to provide an ultraviolet ray transmitting glass composition that can be joined to common commercial soda-lime silica glass.

A glass article of the present invention makes use of the above-mentioned ultraviolet ray transmitting glass composition of the present invention. The present invention makes it possible to provide a glass article that has a high ultraviolet ray transmittance relative to a wavelength of 260 nm, fewer remaining bubbles and a small load on the environment, and can be joined to common commercial soda-lime silica glass. Accordingly, the present invention makes it possible to provide inexpensively, for example, bioanalytical devices that utilize ultraviolet rays.

DESCRIPTION OF THE INVENTION

Figure 1:
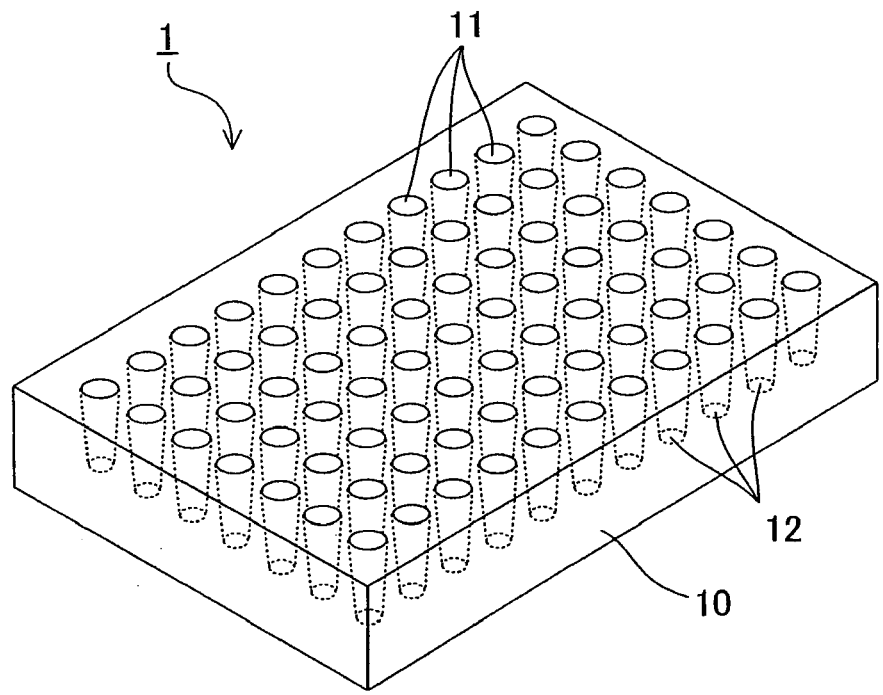
FIG. 1 is a perspective view showing an example of the microplate including an ultraviolet ray transmitting glass composition of the present invention.

The ultraviolet ray transmitting glass composition of the present invention includes, in terms of mass % or mass ppm:
60 to 79% $SiO_2$;
0 to 1% $B_2O_3$;
exceeded 0% but not more than 20% $Al_2O_3$;
0 to 10% $Li_2O$;
5 to 20% $Na_2O$;
0 to 15% $K_2O$;
0 to 10% MgO;
0 to 10% CaO;
0 to 15% SrO;
0 to 2% refining agent;
2 to 20 ppm T-$Fe_2O_3$; and
0 to 200 ppm $TiO_2$.

The above-mentioned ultraviolet ray transmitting glass composition of the present invention may consist essentially of the following components, in terms of mass % or mass ppm:
60 to 79% $SiO_2$;
0 to 1% $B_2O_3$;
exceeded 0% but not more than 20% $Al_2O_3$;
0 to 10% $Li_2O$;
5 to 20% $Na_2O$;
0 to 15% $K_2O$;
0 to 10% MgO;
0 to 10% CaO;
0 to 15% SrO;
0 to 2% refining agent;
2 to 20 ppm T-$Fe_2O_3$; and
0 to 200 ppm $TiO_2$.

In the present description, "consist essentially of" means that the glass composition does not contain any components other than those indicated, or even when the glass composition contains components other than those indicated, the contents of components other than the indicated components are at a level of incorporation as an impurity, and specifically, it means less than 0.1 mass % and preferably less than 200 mass ppm.

The ultraviolet ray transmitting glass composition of the present invention may consist essentially of the following components, in terms of mass % or mass ppm:
60 to 79% $SiO_2$;
0 to 1% $B_2O_3$;
1 to 20% $Al_2O_3$;
0 to 10% $Li_2O$;
5 to 20% $Na_2O$;
0 to 15% $K_2O$;
0 to 10% MgO;
0 to 10% CaO;
0 to 15% SrO;
0 to 2% refining agent;
2 to 20 ppm T-$Fe_2O_3$; and
0 to 200 ppm $TiO_2$.

The ultraviolet ray transmitting glass composition of the present invention may consist essentially of the following components, in terms of mass % or mass ppm:
60 to 79% $SiO_2$;
0 to 1% $B_2O_3$;
1 to 20% $Al_2O_3$;
0 to 10% $Li_2O$;
5 to 16% $Na_2O$;
0 to 15% $K_2O$;
0 to 10% MgO;
0 to 10% CaO;
0 to 15% SrO;
0 to 2% refining agent;
2 to 20 ppm T-$Fe_2O_3$; and
0 to 200 ppm $TiO_2$.

The ultraviolet ray transmitting glass composition of the present invention may consist essentially of the following components, in terms of mass % or mass ppm:
65 to 75% $SiO_2$;
0 to 1% $B_2O_3$;
1 to 5% $Al_2O_3$;
0 to 1% $Li_2O$;
10 to 16% $Na_2O$;
0 to 3% $K_2O$;
0.5 to 5% MgO;
1 to 8% CaO;
0 to 1% SrO;
0 to 2% refining agent;
2 to 20 ppm T-$Fe_2O_3$; and
0 to 200 ppm $TiO_2$.

The ultraviolet ray transmitting glass composition of the present invention may consist essentially of the following components, in terms of mass % or mass ppm:
60 to 70% $SiO_2$;
14 to 20% $Al_2O_3$;

3 to 6% $Li_2O$;
7 to 13% $Na_2O$;
0 to 1% $K_2O$;
0.5 to 3% MgO;
1 to 6% CaO;
0 to 1% SrO;
0 to 2% refining agent;
2 to 20 ppm T-$Fe_2O_3$; and
0 to 200 ppm $TiO_2$.

In the ultraviolet ray transmitting glass composition of the present invention, the content of T-$Fe_2O_3$ may be 2 to 10 mass ppm, or 2 to 6 mass ppm. The content of T-$Fe_2O_3$ is preferably 2 to 4 mass ppm to achieve a higher ultraviolet ray transmittance.

In the ultraviolet ray transmitting glass composition, the content of a refining agent may exceed 0 mass %.

The ultraviolet ray transmitting glass composition of the present invention may include at least one selected from the group of $SO_3$, Cl and F as the refining agent, and the contents of the components, in terms of mass %, may be as follows:
0 to 1% $SO_3$;
0 to 1% Cl; and
0 to 1% F. In this case, the ultraviolet ray transmitting glass composition of the present invention includes $SO_3$ as the refining agent preferably. The content of $SO_3$, in terms of mass %, preferably exceeds 0% but is not more than 1% (more preferably 0.01% to 1%, further preferably 0.1% to 1%). The ultraviolet ray transmitting glass composition can include Cl as the refining agent. In this case, it is preferable that the content of Cl exceeds 0% but is less than 0.1%.

When the ultraviolet ray transmitting glass composition of the present invention is used for, for example, bioanalytical devices utilizing ultraviolet rays, it is preferable that the ultraviolet ray transmitting glass composition of the present invention has an ultraviolet ray transmittance of at least 50% relative to a wavelength of 260 nm when formed into a glass sheet having a thickness of 1 mm. This is because the ultraviolet rays utilized for the bioanalytical devices have a wavelength around 260 nm. In this case, the ultraviolet ray transmittance is preferably at least 70%, and more preferably at least 80% to achieve higher detection accuracy.

The ultraviolet ray transmitting glass composition of the present invention preferably has an average linear thermal expansion coefficient in a range of 50 to 350° C. of 80 to $100 \times 10^{-7}$/° C. in consideration of the case in which the ultraviolet ray transmitting glass composition is used with (or joined to) other glass.

Reasons for the limitations in the components in the ultraviolet ray transmitting glass composition of the present invention are described below. It should be noted that mass % and mass ppm may be abbreviated simply as % and ppm respectively in the following description.

($SiO_2$)

$SiO_2$ is an essential component that forms a glass skeleton. When the content of $SiO_2$ is less than 60%, the glass has deteriorated chemical durability. On the other hand, when the content of $SiO_2$ is more than 79%, the viscosity of the glass melt becomes so high that the refining of the glass melt becomes difficult. Thus, the content of $SiO_2$ needs to be 60% to 79%. The content of $SiO_2$ is preferably at least 63%, and more preferably at least 65%. In addition, the content of $SiO_2$ is preferably 75% or less, and more preferably 70% or less.

($B_2O_3$)

$B_2O_3$ is an optional component. $B_2O_3$ is effective in causing the above-mentioned nonbridging oxygen to disappear and improving the chemical durability of a glass composition. However, when the content of $B_2O_3$ in the glass composition is excessively large, cords may occur in glass articles because of vaporizing of $B_2O_3$ from a glass melt in melting the glass composition and the melting furnace may be damaged by the volatilized boron compounds. Thus, in order to prevent the above-mentioned problems, the content of $B_2O_3$ needs to be 1% or less, and it is preferable that the glass composition is substantially free from $B_2O_3$.

($Al_2O_3$)

$Al_2O_3$ is an essential component. Like $B_2O_3$, $Al_2O_3$ is effective in causing the above-mentioned nonbridging oxygen to disappear and improving chemical durability of a glass composition. However, $Al_2O_3$, unlike $B_2O_3$, is effective in increasing the viscosity of the glass melt. Therefore, when the content of $Al_2O_3$ exceeds 20%, it is difficult to melt the glass composition. Thus, the content of $Al_2O_3$ needs to exceed 0% but is not more than 20%, and is preferably 1 to 20%. A more preferable range of the content of $Al_2O_3$ is 1 to 5% or 14 to 20%.

($Na_2O$)

$Na_2O$ is an essential component. $Na_2O$ is effective in decreasing the viscosity of the glass melt and improving the meltability of the glass melt. In addition, $Na_2O$ is effective in increasing the thermal expansion coefficient. However, $Na_2O$ contained in a glass composition may cause the nonbridging oxygen to occur in the glass composition. The nonbridging oxygen causes the transmittance, particularly relative to a wavelength in the range of 240 nm or less, to decrease. In addition, when the content of $Na_2O$ is excessively large, the chemical durability of the glass articles may be deteriorated. Thus, the content of $Na_2O$ needs to be 5 to 20%, and is preferably 16% or less. Moreover, the content of $Na_2O$ is more preferably 10 to 16%, and further preferably 7 to 13% in order to adjust the thermal expansion coefficient of the glass composition of the present invention to an approximate value of that of common commercial soda-lime silica glass.

($K_2O$)

$K_2O$ is an optional component. Like $Na_2O$, $K_2O$ is effective in decreasing the viscosity of the glass melt and improving the meltability of the glass, and in increasing the thermal expansion coefficient. On the other hand, $K_2O$ contained in a glass composition may cause the nonbridging oxygen to occur in the glass composition and decrease the transmittance, particularly relative to a wavelength in the range of 240 nm or less. In addition, when the content of $K_2O$ is excessively large, the chemical durability of the glass articles may be deteriorated. Thus, the content of $K_2O$ needs to be 15% or less, and is preferably 3% or less and further preferably 1% or less.

($Li_2O$)

$Li_2O$ is an optional component that has an effect of decreasing the viscosity of the glass melt and improving the meltability of the glass. However, $Li_2O$ contained in a glass composition may cause the nonbridging oxygen to occur in the glass composition. The nonbridging oxygen causes the transmittance, particularly relative to a wavelength in the range of 240 nm or less, to decrease. In addition, when the content of $Li_2O$ is excessively large, the chemical durability of the glass articles may be deteriorated. Thus, the content of $Li_2O$ needs to be 10% or less, and is preferably 6% or less. It is more preferable that the content of $Li_2O$ is 1% or less when the content of $Al_2O_3$ is 1 to 5% and the content of $Li_2O$ is 3 to 6% when the content of $Al_2O_3$ is 14 to 20%.

(Total Amount of Na$_2$O, K$_2$O and Li$_2$O)

As described above, when the contents of Na$_2$O, K$_2$O and/or Li$_2$O are excessively large, undesirable effects, such as decreasing the ultraviolet ray transmittance or deteriorating the chemical durability, are caused. Therefore, the total amount of Na$_2$O, K$_2$O and Li$_2$O is preferably 25% or less, more preferably 20% or less and further preferably 18% or less.

(MgO and CaO)

MgO and CaO are optional components. They, however, are components that preferably are contained. MgO and CaO are effective in decreasing the viscosity of the glass melt and improving the meltability of the glass. In addition, MgO and CaO are effective in improving the chemical durability of a glass composition. When the glass composition includes at least 0.5% MgO or at least 1% CaO, the above-mentioned effects can be obtained easily. However, when the content of MgO or CaO exceeds 10%, devitrification tends to be generated in the glass composition and it is difficult to form glass articles from the glass melt. It should be noted that a glass composition that includes both MgO and CaO can improve devitrification resistance thereof. Thus, the content of MgO needs to be 10% or less. In addition, the content of MgO is preferably at least 0.5%, or 5% or less, and more preferably 3% or less. The content of CaO needs to be 10% or less. In addition, the content of CaO is preferably at least 1%, or 8% or less, and more preferably 6% or less.

(SrO)

SrO is an optional component. Like MgO and CaO, SrO is effective in decreasing the viscosity of the glass melt and improving the meltability of the glass, and in improving the chemical durability of the glass composition. However, raw material of SrO is expensive. Therefore, when the content of SrO in the glass composition is excessively large, glass articles (for example, the above-mentioned bioanalytical devices) using the glass composition are expensive. SrO is a component having high density among components that compose the glass composition of the present invention. Therefore, when the content of SrO is excessively large, a SrO component goes to the bottom of the glass melt in melting glass, particularly in the early stage of melting a batch. It may cause inhomogeneity of the glass melt. Thus, the content of SrO needs to be 15% or less, and is preferably 1% or less. In addition, it is preferable that the glass composition is substantially free from SrO.

(Iron Oxides)

Iron oxides exist in the form of FeO and/or Fe$_2$O$_3$ in a glass composition of the present invention. In the present description, the contents of iron oxides are in terms of a total iron oxide content obtained by converting all of iron compounds into Fe$_2$O$_3$, and the total iron oxide content is denoted in T-Fe$_2$O$_3$. On the other hand, the content of FeO is expressed in percentage (mass %) of the amount of FeO converted into Fe$_2$O$_3$ in T-Fe$_2$O$_3$. The content of FeO is indicated by FeO ratio.

Fe$_2$O$_3$ absorbs ultraviolet rays strongly. Thus, T-Fe$_2$O$_3$ is preferably smaller in the glass composition. When the content of T-Fe$_2$O$_3$ is 20 ppm or less, it is easy to adjust an ultraviolet ray transmittance relative to a wavelength of 260 nm when being formed into a glass sheet having a thickness of 1 mm in the range of at least 50%. On the other hand, when T-Fe$_2$O$_3$ is excessively small, refinement of the glass melt may be deteriorated. And then, glass articles made from the glass melt may have fine bubbles remaining and defects may occur in the glass articles. When the content of T-Fe$_2$O$_3$ is at least 2 ppm, refinement of the glass melt is improved considerably. Thus, the content of T-Fe$_2$O$_3$ is preferably 2 to 20 ppm. In order to adjust easily an ultraviolet ray transmittance relative to a wavelength of 260 nm when being formed into a glass sheet having a thickness of 1 mm in the range of at least 80%, it is more preferable that the the content of T-Fe$_2$O$_3$ is 4 ppm or less.

In addition, when FeO ratio is at least 31%, the ultraviolet ray transmittance relative to a wavelength of 260 nm can be higher.

(TiO$_2$)

TiO$_2$ also absorbs ultraviolet rays strongly. Thus, the content of TiO$_2$ in a glass composition is preferably smaller. TiO$_2$ needs to be 200 ppm or less in order to achieve an ultraviolet ray transmittance of at least 50% relative to a wavelength of 260 nm when being formed into a glass sheet having a thickness of 1 mm. In order to achieve a higher ultraviolet ray transmittance, it is preferable that the content of TiO$_2$ is 50 ppm or less.

As described above, Fe$_2$O$_3$ and TiO$_2$ are components that absorb ultraviolet rays strongly. Thus, they are in terms of ppm scale unlike other components.

(Other Components (Impurity))

It is preferable that the contents of colored components, ultraviolet-absorbing components and components that cause fluorescence are smaller. Examples of the above-mentioned components are oxides having at least one selected from the group of V, Cr, Mn, Co, Ni, Cu, Sn, Sb, Te, As, Se, Pb, Bi, Ce and rare earth elements as cation, Au, Rh and Pt. In order to achieve an ultraviolet ray transmittance of at least 50% relative to a wavelength of 260 nm when formed into a glass sheet having a thickness of 1 mm, the total amount of the above-mentioned components needs to be 200 ppm or less.

(Refining Agent and Remaining Amount Thereof)

In a glass composition of the present invention, refining agent components can be contained at most at 2%. Examples of the refining agent components are SO$_3$, Cl and F. SO$_3$ is preferable among these refining agent components. Particularly, in order to obtain a high refining effect, it is preferable that a reducing agent, such as carbon, is added to a batch for making a glass composition, and the content of SO$_3$ is 0.01 to 1%. It is more preferable that the content of SO$_3$ is 0.1 to 0.5%.

Hereafter, a microplate (a bioanalytical device) as an example of a glass article of the present invention is described with reference to the drawings.

Figure 2:
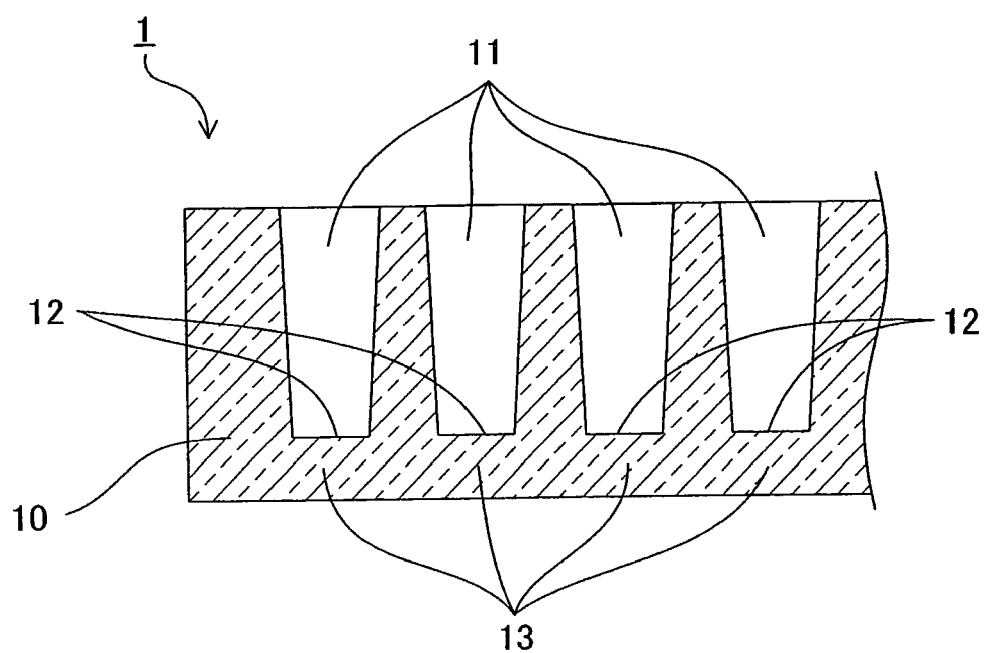
FIG. 2 is a partial cross-sectional view of the microplate shown in FIG. 1.

In a microplate 1 shown in FIGS. 1 and 2, concave parts 11 for retaining a sample to be analyzed or cultured are formed in the surface of a glass plate 10 made of an ultraviolet ray transmitting glass composition of the present invention. The concave parts 11 are identical in shape to one another and are arranged in the surface of the glass plate 10 in the form of a matrix. Ultraviolet rays with which the sample retained in the concave parts 11 is irradiated from the opening side of the concave parts 11 pass through the sample as well as the portions (light transmitting parts) 13 that adjoin the bottom portions 12 of the concave parts 11. The light transmitting parts 13 of the microplate 1 are formed of the ultraviolet ray transmitting glass composition. Accordingly, measurement is easy to carry out with high accuracy. Furthermore, since all the portions that adjoin the concave parts 11 are formed of the ultraviolet ray transmitting glass composition, there is no concern about the resistance to organic solvents.

Figure 3:
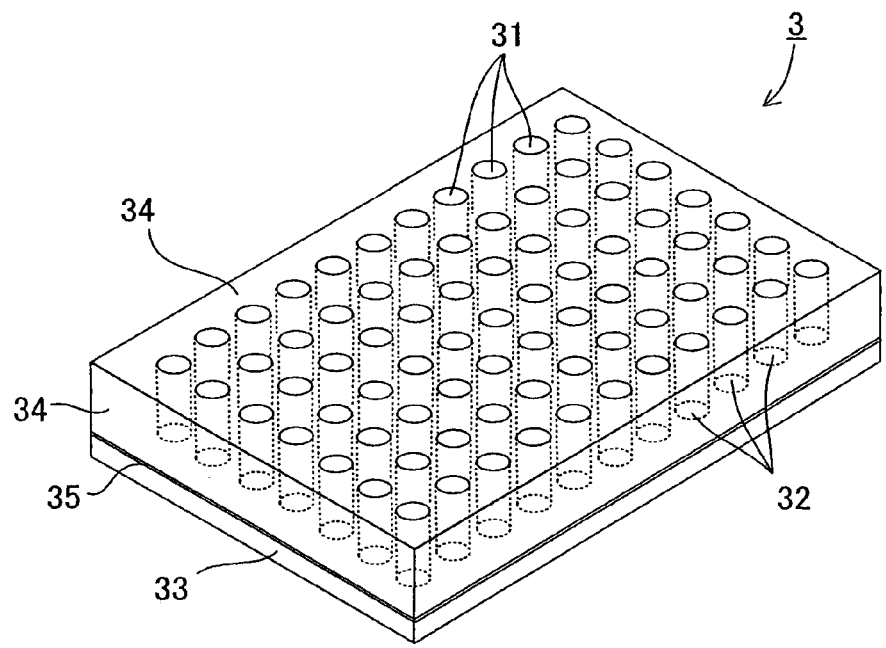
FIG. 3 is a perspective view showing another example of the microplate including an ultraviolet ray transmitting glass composition of the present invention.
Figure 4:
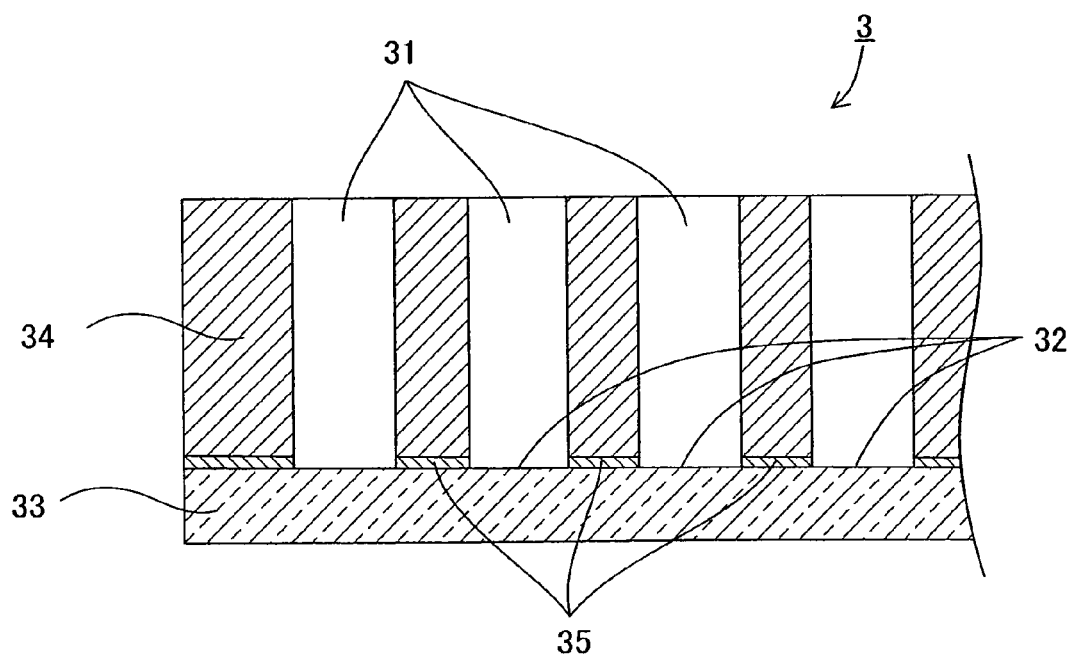
FIG. 4 is a partial cross-sectional view of the microplate shown in FIG. 3.

In a microplate 3 shown in FIGS. 3 and 4, a bottom plate 33 that adjoins bottom portions 32 of concave parts 31 and a molded member 34 that adjoins side portions of the concave parts 31 are joined to each other with a joint agent 35. A plate-like member formed of ultraviolet ray transmitting glass composition of the present invention is used for the bottom plate 33. On the other hand, glass, for example, soda-lime silica glass, in which through holes to serve as the concave parts 31 are formed, is used for the molded member 34. A low-melting glass may be used for the joint agent 35, for example. The microplate 3 has a logical configuration in which the ultraviolet ray transmitting glass composition can be used for the part where importance is attached to the ultraviolet ray transmittance while a general-purpose material can be used for the part that needs to be processed. Even when the ultraviolet ray transmitting glass of the present invention and soda-lime silica glass are joined to each other by a method including heating, the problem that results from the difference in thermal expansion coefficient tends not to occur.

Figure 5:
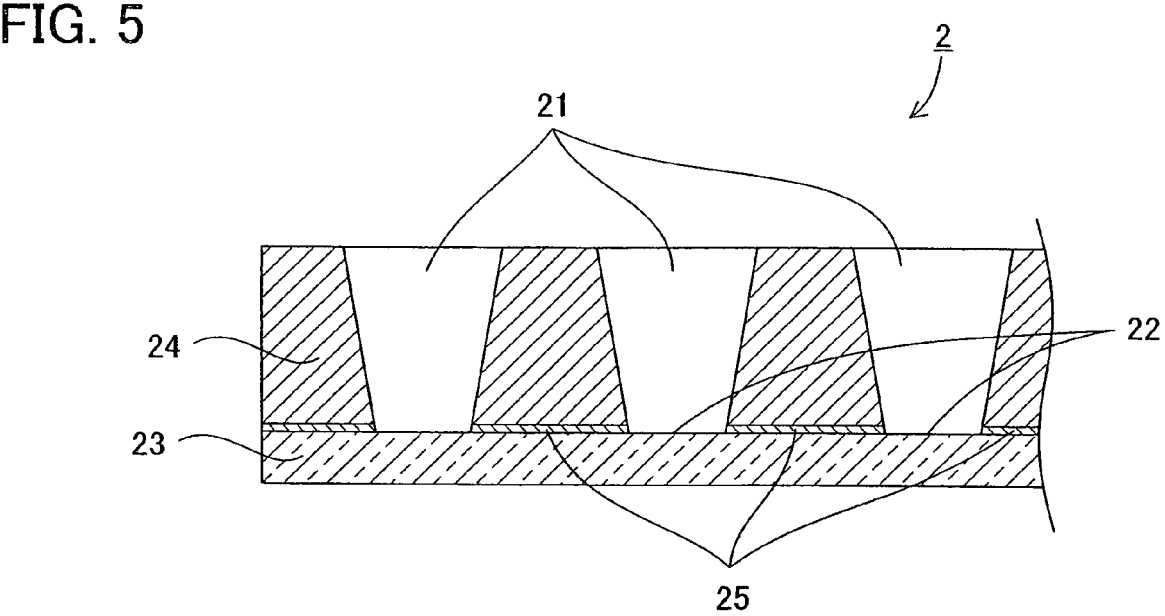
FIG. 5 is a partial cross-sectional view of still another example of the microplate including an ultraviolet ray transmitting glass composition of the present invention.

The shape of the concave parts is not particularly limited. It may be a shape of truncated cone (whose cross section is trapezoid) as shown in FIGS. 1 and 2 or may be a shape of rectangular parallelepiped (whose cross section is rectangle) as shown in FIGS. 3 and 4. From the viewpoint of facilitating the washing that is required when it is used repeatedly, an excellent shape of the concave part is one in which the area of the transverse section thereof decreases towards the bottom portion 12 like the former, the concave parts 11. In consideration of this, concave parts 21 with a shape of truncated cone may be formed in a microplate 2 including a bottom plate 23, a molded member 24, and a joint agent 25 (see FIG. 5).

Then, the ultraviolet ray transmitting glass composition of the present invention is described in detail with Examples. The present invention, however, is not limited to the following description.

Examples 1 to 8, and Comparative Examples 1 and 2

In Examples 1 to 8, and Comparative Examples 1 and 2, the relationship between the contents of T-$Fe_2O_3$ and $TiO_2$ in the glass composition, and the ultraviolet ray transmittance relative to a wavelength of 260 nm when being formed into a glass sheet having a thickness of 1 mm, the thermal expansion coefficient in a range of 50° C. to 350° C., and etc. were studied.

(Fabrication of Glass Sample)

Each glass sample was fabricated by following the procedures. High purity silicon dioxide, dialuminum trioxide, diboron trioxide, lithium carbonate, sodium carbonate, potassium carbonate, magnesium oxide, calcium carbonate, ferric oxide, titanium oxide, strontium carbonate, sodium sulfate, sodium chloride and carbon are used as raw materials for glass components. The raw materials were mixed according to a predetermined ratio in order to provide glass compositions shown in Table 1 and the amount of each glass melt was 400 g. Accordingly, a raw material for glass (hereinafter, referred to as a batch) was prepared.

The prepared batch was melted and refined in a platinum crucible. Firstly, the crucible was maintained for four hours in an electric furnace set at a temperature of 1450° C. to melt and refine the batch. After that, the glass melt was poured on an iron plate outside the furnace so that the thickness thereof was about 6 mm and it was cooled and solidified to obtain the glass body. The glass body subsequently was subjected to an operation of annealing. The annealing was carried out by keeping the glass body in another electric furnace set at a temperature of 650° C. for 30 minutes and then turning off the electric furnace to cool down to room temperature. The glass body that underwent the operation of annealing was made a glass sample.

(Measurement of Ultraviolet Ray Transmittance)

With respect to each of glass samples of Examples and Comparative Examples, the ultraviolet ray transmittance was measured in the following way. Firstly, each of the above-mentioned glass samples was cut, ground and optically polished using a common glass processing technique. Accordingly, a glass specimen in a square shape having a side of 3 cm and a thickness of 1 mm was formed. Both main surfaces of the glass specimen were optically polished. The transmittance of the glass specimen was measured using a visible-ultraviolet spectrophotometer (a product of Shimadzu Corporation, UV-3100PC). The measurement results are shown in Table 1. It should be noted that the transmittance relative to a wavelength of 260 nm is referred to as an ultraviolet ray transmittance in the present description.

Figure 6:
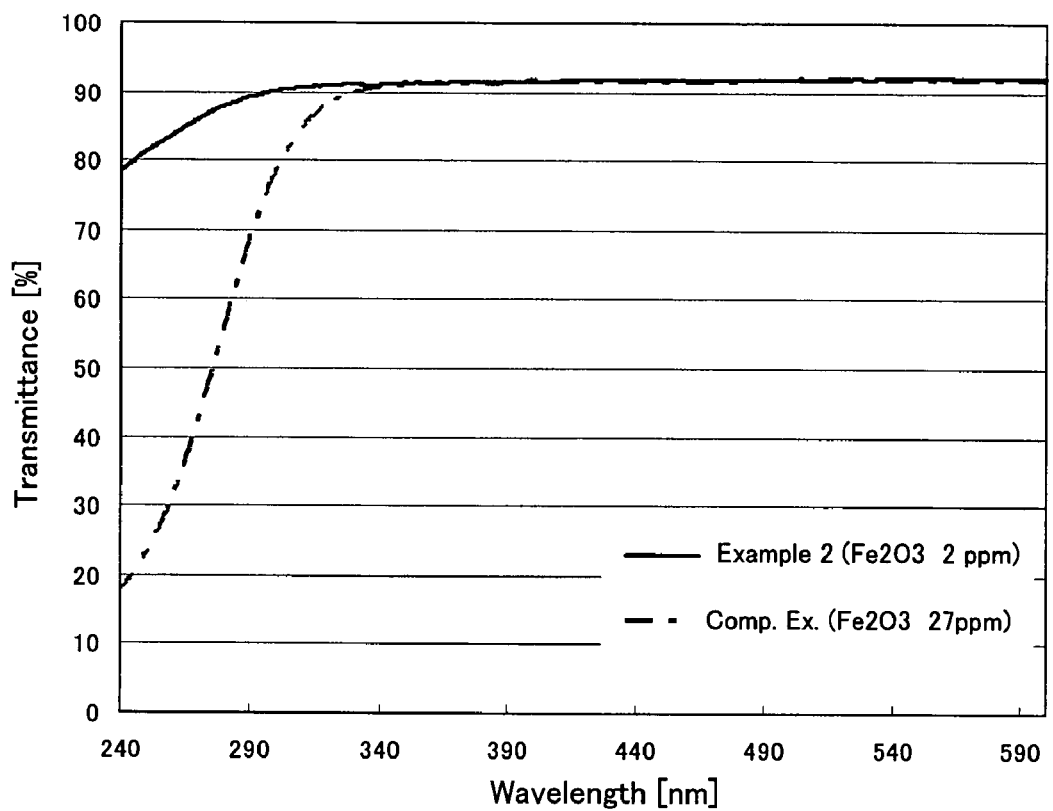
FIG. 6 is a diagram showing spectral transmission curves of the glass compositions in Example 1 and Comparative Example 1 when each of the glass compositions is formed into a glass sheet having a thickness of 1 mm.

With respect to each of Example 2 and Comparative Example 1, the transmittance relative to a wavelength in a range of 240 to 600 nm was measured using the same device. The spectral transmittance curves are shown in FIG. 6.

(Measurement of Thermal Expansion Coefficient and Glass Transition Temperature)

A glass specimen for measurement of thermal expansion coefficient in a cylinder shape having a diameter of 5 mm and a length of 15 mm was made from the glass sample using a common glass processing technique. The thermal expansion coefficient and the glass transition temperature of the glass specimen were measured by using a differential thermomechanical analyzer (Thermoflex TMA 8140, manufactured by Rigaku Corporation). These measurement results also are shown in Table 1.

(Devitrification Test)

With respect to each of Examples and Comparative Examples, the devitrification temperature was measured in the following way. Firstly, the above-mentioned glass sample was crushed, and about 40 g of glass grains that passed through a sieve of 2380 μm and remained on a sieve of 1000 μm were prepared. The glass grains were cleaned ultrasonically in ethanol, and then dried in a thermostat to make them the test sample for the devitrification test. 25 g of each test sample were weighed and put into a platinum boat of 12 mm in width, 200 mm in length and 10 mm in depth. The platinum boat subsequently was put in an electric furnace having a temperature gradient from 930° C. to 1180° C. The platinum boat was kept in the furnace for two hours, and then the platinum boat was taken out of the furnace and was left to cool down to room temperature. The devitrification generated inside the glass on the platinum boat was observed using an optical microscope of a magnification of 40 times, and the maximum temperature at which the devitrification was observed was defined as the devitrification temperature. These measurement results also are shown in Table 1.

(Measurement of Viscosity of Glass Melt)

A melting temperature and a working temperature of the above-mentioned glass sample were measured using a platinum ball pulling type automated viscometer. The melting temperature is a temperature at which the viscosity η, in terms of poise, of a glass melt satisfies log η=2. The working temperature is a temperature at which the viscosity η, in terms of poise, of a glass melt satisfies log η=4. These measurement results also are shown in Table 1.

TABLE 1

|  |  | Ex. 1 | Ex. 2 | Ex. 3 | Ex. 4 | Ex. 5 | Ex. 6 | Ex. 7 | Ex. 8 | Ex. 9 | C. Ex. 1 | C. Ex. 2 |
|---|---|---|---|---|---|---|---|---|---|---|---|---|
| Composition (mass %) | $SiO_2$ | 70.7 | 72.1 | 72.1 | 63.6 | 65.4 | 68.8 | 70.8 | 70.7 | 72.1 | 72.1 | 72.1 |
| | $Al_2O_3$ | 2.4 | 2.0 | 2.0 | 16.2 | 15.3 | 5.0 | 0.5 | 1.6 | 2.0 | 2.0 | 2.0 |
| | $B_2O_3$ | 0 | 0 | 0 | 0 | 0 | 0 | 0.5 | 0 | 0 | 0 | 0 |
| | $Li_2O$ | 0 | 0 | 0 | 3.4 | 3.0 | 0 | 0 | 1.5 | 0 | 0 | 0 |
| | $Na_2O$ | 16.0 | 13.4 | 13.4 | 10.5 | 9.0 | 15.0 | 14.5 | 12.0 | 13.4 | 13.4 | 13.4 |
| | $K_2O$ | 1.5 | 1.1 | 1.1 | 0.4 | 0 | 1.0 | 1.0 | 1.0 | 1.1 | 1.1 | 1.1 |
| | $MgO$ | 3.3 | 4.0 | 4.0 | 2.0 | 2.9 | 3.0 | 5.0 | 5.0 | 4.0 | 4.0 | 4.0 |
| | $CaO$ | 5.0 | 7.9 | 7.9 | 3.8 | 3.3 | 6.0 | 7.5 | 8.0 | 7.9 | 7.9 | 7.9 |
| | $SrO$ | 0 | 0 | 0 | 0 | 0.9 | 1.0 | 0 | 0 | 0 | 0 | 0 |
| | $SO_3$ | 0.26 | 0.22 | 0.23 | 0.17 | 0.16 | 0.22 | 0.21 | 0.24 | 0.19 | 0.23 | 0.22 |
| | Cl | 0 | 0 | 0 | 0 | 0.08 | 0.01 | 0 | 0 | 0 | 0 | 0 |
| | T·$Fe_2O_3$ (mass ppm) | 2.0 | 2.0 | 5.0 | 5.0 | 16 | 4.0 | 4.0 | 4.0 | 5.0 | 27 | 2.0 |
| | $TiO_2$ (mass ppm) | 2.0 | 2.0 | 6.0 | 5.0 | 4.0 | 3.0 | 3.0 | 3.0 | 6.0 | 2.0 | 270 |
| Melting Condition | | 1450° C. 4 h | 1450° C. 4 h | 1450° C. 4 h | 1450° C. 4 h | 1450° C. 4 h | 1450° C. 4 h | 1450° C. 4 h | 1450° C. 4 h | 1550° C. 4 h | 1450° C. 4 h | 1450° C. 4 h |
| Characteristic Temperature (° C.) | Melting Temperature ($\log\eta = 2$) | 1480 | 1472 | 1472 | 1514 | 1545 | 1457 | 1385 | 1366 | 1472 | 1472 | 1472 |
| | Working Temperature ($\log\eta = 4$) | 1040 | 1041 | 1041 | 1040 | 1067 | 1020 | 981 | 952 | 1041 | 1041 | 1041 |
| | Devitrification Temperature $T_L$ | 969 | 1038 | 1038 | 1004 | 1047 | 801 | 929 | 1035 | 1038 | 1038 | 1038 |
| | Glass Transition Temperature $T_g$ | 528 | 550 | 550 | 517 | 536 | 548 | 546 | 512 | 550 | 550 | 550 |
| Density (g/cm³) | | 2.48 | 2.49 | 2.49 | 2.46 | 2.48 | 2.50 | 2.50 | 2.51 | 2.49 | 2.49 | 2.49 |
| Average Thermal Expansion Coefficient in the range of 50 to 350° C. ($\times 10^{-7}$/° C.) | | 99 | 88 | 88 | 90 | 78 | 88 | 90 | 92 | 88 | 88 | 88 |
| Transmittance relative to a wavelength of 260 nm when having a thickness of 1 mm (%) | | 84 | 84 | 73 | 74 | 60 | 82 | 86 | 85 | 68 | 31 | 29 |

Comparison Between Examples 1 to 8, and Comparative Examples 1 and 2

As shown in Table 1, in comparison between Examples 1 to 8, and Comparative Examples 1 and 2, each of Examples 1 to 8 in which the content of T-$Fe_2O_3$ is 20 ppm or less and the content of $TiO_2$ is 200 ppm or less had a transmittance of at least 60% relative to a wavelength of 260 nm when having a thickness of 1 mm. Particularly, each of Examples 1, 2 and 6 to 8 had a transmittance of at least 80%. Accordingly, it was found out that the ultraviolet ray transmitting glass composition of the present invention had a considerably high ultraviolet ray transmittance.

Example 9

A glass composition in Example 9 was the same as that in Example 3, but a melting condition in fabricating a glass sample of Example 9 was changed from that of Example 3.

The glass sample of Example 9 was fabricated in the same manner as the above-mentioned Examples 1 to 8, except that the temperature in melting and refining a batch was set at 1550° C. The ultraviolet ray transmittance, the thermal expansion coefficient, the glass transition temperature, the devitrification temperature, the melting temperature and the working temperature were measured in the same manner as in Examples 1 to 8. These measurement results are shown in Table 1.

The thermal expansion coefficient, the glass transition temperature, the devitrification temperature, the melting temperature and the working temperature of Example 9 were the same as those of Example 3. The ultraviolet ray transmittance of Example 9, however, was 5% less than that of Example 3.

It has been known that when a platinum crucible is used in melting the glass, platinum is melted out from the crucible and mixed into the glass melt. Furthermore, it has been known that platinum in the glass causes the glass to absorb ultraviolet rays and scatter light. The present inventors consider that since the melting and refining temperature of the batch in Example 9 was higher than that in Example 3, the content of platinum in the glass sample of Example 9 was more than that of Example 3 and therefore the ultraviolet ray transmittance in Example 9 was deteriorated.

Examples 10 to 15, and Comparative Examples 3 and 4

In each of Examples 10 to 15, and Comparative Examples 3 and 4, the relationship between T-$Fe_2O_3$, the redox state of the batch and FeO ratio, and the ultraviolet ray transmittance relative to a wavelength of 260 nm when having a thickness of 1 mm and the refinement of the glass melt were considered.

Each of glass samples having glass compositions shown in Table 2 was fabricated in the same method as in Example 1 to 8. The redox state of the batch was evaluated using the carbon number as an indicator. The method of the evaluation using the carbon number was described by W. H. Manring, W. Hopkins and et al. in "The Glass Industry, Vol. 39, No. 5, pp. 139 to 142 and 170, 1958." In Examples 10 to 15, the carbon number can be obtained by the following calculating formula using the contents of sodium nitrate and carbon.

Carbon Number=(the mass ratio of sodium nitrate to silicon dioxide in the batch)×1340−(the mass ratio of carbon to silicon dioxide in the batch)×32000

As shown in this formula, the higher the reducing ability of the batch, the smaller the carbon number.

The ultraviolet ray transmittance of the obtained glass sample was measured in the same method as in the above-mentioned Examples. The measurement results are shown in Table 2.

FeO ratio of the glass sample also was obtained as an indicator of the reducing ability. The results are shown in Table 2. It should be noted that T-$Fe_2O_3$ was so small that the FeO ratio could not be obtained in each of Examples 12 to 15.

(Evaluation of Refinement)

In each of Examples and Comparative Examples, the refinement was evaluated as follows.

A batch was prepared in order to have a glass composition shown in Table 2 and the amount of each glass melt was 50 g.

The prepared batch was melted and refined in the same method as in the above-mentioned Examples 1 to 8. Then, the glass melt was not poured, and was cooled down to room temperature in the platinum crucible. The solidified glass was taken out from the platinum crucible, and the glass was used as a sample for evaluation of refinement.

The sample for evaluation of refinement was observed using an optical microscope of a magnification of 40 times, and the number of bubbles in the field of view was counted. Using the counted number of bubbles, the thickness of the sample for evaluation of refinement, the view area in the optical microscope and the density of the sample, the number of bubbles per 1 g of the sample for evaluation of refinement was calculated. The result was shown in Table 2.

TABLE 2

| | | Ex. 10 | Ex. 11 | Ex. 12 | Ex. 13 | Ex. 14 | Ex. 15 | C. Ex. 3 | C. Ex. 4 |
|---|---|---|---|---|---|---|---|---|---|
| Composition (mass %) | $SiO_2$ | 72.1 | 72.1 | 72.1 | 72.1 | 72.1 | 72.1 | 72.1 | 72.1 |
| | $Al_2O_3$ | 2.0 | 2.0 | 2.0 | 2.0 | 2.0 | 2.0 | 2.0 | 2.0 |
| | $Li_2O$ | 0 | 0 | 0 | 0 | 0 | 0 | 0 | 0 |
| | $Na_2O$ | 13.4 | 13.4 | 13.4 | 13.4 | 13.4 | 13.4 | 13.4 | 13.4 |
| | $K_2O$ | 1.1 | 1.1 | 1.1 | 1.1 | 1.1 | 1.1 | 1.1 | 1.1 |
| | MgO | 4.0 | 4.0 | 4.0 | 4.0 | 4.0 | 4.0 | 4.0 | 4.0 |
| | CaO | 7.9 | 7.9 | 7.9 | 7.9 | 7.9 | 7.9 | 7.9 | 7.9 |
| | $SO_3$ | 0.22 | 0.06 | 0.23 | 0.06 | 0.22 | 0.06 | 0.21 | 0.06 |
| | T-$Fe_2O_3$ (mass ppm) | 20 | 20 | 5.0 | 5.0 | 2.0 | 2.0 | 1.5 | 1.5 |
| | $TiO_2$ (mass ppm) | 0 | 0 | 0 | 0 | 0 | 0 | 0 | 0 |
| Carbon Number | | 6.67 | −0.51 | 6.67 | −0.51 | 6.67 | −0.51 | 6.67 | −0.51 |
| FeO ratio (%) | | 33 | 48 | — | — | — | — | — | — |
| Density (g/cm³) | | 2.49 | 2.49 | 2.49 | 2.49 | 2.49 | 2.49 | 2.49 | 2.49 |
| Transmittance relative to a wavelength of 260 nm when having a thickness of 1 mm (%) | | 51 | 54 | 74 | 78 | 85 | 85 | 86 | 86 |
| Number of bubbles (per 1 g) | | 150 | 0 | 120 | 0 | 120 | 60 | 200 | 250 |

Comparison Between Examples 10 to 15, and Comparative Examples 3 and 4

As shown in Table 2, in comparison between Examples 10 to 15, and Comparative Examples 3 and 4, it is found out that when the content of T-$Fe_2O_3$ is 2 ppm or more, the sample in which the number of bubbles is smaller can be obtained.

In addition, from the results shown in Table 2, the following are found out by considering the relationship between the carbon number, and the ultraviolet ray transmittance and the number of bubbles in Examples 10 to 15 and Comparative Examples 3 and 4. The sample in which the number of bubbles is smaller can be obtained when the reducing ability on the batch is increased. FeO ratio and the ultraviolet ray transmittance can be higher when the reducing ability of the batch is increased.

Therefore, in the ultraviolet ray transmitting glass composition of the present invention, since T-$Fe_2O_3$ is in an appropriate range, a glass composition having both an extremely high ultraviolet ray transmittance and excellent refinement can be provided.

INDUSTRIAL APPLICABILITY

The glass composition of the present invention can be used for an application requiring a thermal expansion coefficient nearly equal to that of a common soda-lime silica glass and a high ultraviolet ray transparency. The glass composition can be used for, for example, an ultraviolet ray transmitting window.

The invention claimed is:

1. An ultraviolet ray transmitting glass composition consisting essentially of following components, in terms of mass % or mass ppm:
   60 to 79% $SiO_2$;
   0 to 1% $B_2O_3$;
   exceeded 0% but not more than 20% $Al_2O_3$;
   0 to 10% $Li_2O$;
   5 to 20% $Na_2O$;
   0 to 15% $K_2O$;
   0 to 10% MgO;
   0 to 10% CaO;
   0 to 15% SrO;
   0 to 2% refining agent;
   2 to 20 ppm $T\text{-}Fe_2O_3$ (in which $T\text{-}Fe_2O_3$ denotes a total iron oxide content obtained by reducing all of iron compounds to $Fe_2O_3$); and
   0 to 200 ppm $TiO_2$,
   wherein the ultraviolet ray transmitting glass composition has an ultraviolet ray transmittance of at least 50% relative to a wavelength of 260 nm when formed into a glass sheet having a thickness of 1 mm.

2. The ultraviolet ray transmitting glass composition according to claim 1, consisting essentially of the following components, in terms of mass % or mass ppm:
   60 to 79% $SiO_2$;
   0 to 1% $B_2O_3$;
   1 to 20% $Al_2O_3$;
   0 to 10% $Li_2O$;
   5 to 20% $Na_2O$;
   0 to 15% $K_2O$;
   0 to 10% MgO;
   0 to 10% CaO;
   0 to 15% SrO;
   0 to 2% refining agent;
   2 to 20 ppm $T\text{-}Fe_2O_3$ (in which $T\text{-}Fe_2O_3$ denotes a total iron oxide content obtained by reducing all of iron compounds to $Fe_2O_3$); and
   0 to 200 ppm $TiO_2$.

3. The ultraviolet ray transmitting glass composition according to claim 1, consisting essentially of the following components, in terms of mass % or mass ppm:
   60 to 79% $SiO_2$;
   0 to 1% $B_2O_3$;
   1 to 20% $Al_2O_3$;
   0 to 10% $Li_2O$;
   5 to 16% $Na_2O$;
   0 to 15% $K_2O$;
   0 to 10% MgO;
   0 to 10% CaO;
   0 to 15% SrO;
   0 to 2% refining agent;
   2 to 20 ppm $T\text{-}Fe_2O_3$ (in which $T\text{-}Fe_2O_3$ denotes a total iron oxide content obtained by converting all of iron compounds into $Fe_2O_3$); and
   0 to 200 ppm $TiO_2$.

4. The ultraviolet ray transmitting glass composition according to claim 1, consisting essentially of the following components, in terms of mass % or mass ppm:
   65 to 75% $SiO_2$;
   0 to 1% $B_2O_3$;
   1 to 5% $Al_2O_3$;
   0 to 1% $Li_2O$;
   10 to 16% $Na_2O$;
   0 to 3% $K_2O$;
   0.5 to 5% MgO;
   1 to 8% CaO;
   0 to 1% SrO;
   0 to 2% refining agent;
   2 to 20 ppm $T\text{-}Fe_2O_3$ (in which $T\text{-}Fe_2O_3$ denotes a total iron oxide content obtained by converting all of iron compounds into $Fe_2O_3$); and
   0 to 200 ppm $TiO_2$.

5. The ultraviolet ray transmitting glass composition according to claim 1, consisting essentially of the following components, in terms of mass % or mass ppm:
   60 to 70% $SiO_2$;
   14 to 20% $Al_2O_3$;
   3 to 6% $Li_2O$;
   7 to 13% $Na_2O$;
   0 to 1% $K_2O$;
   0.5 to 3% MgO;
   1 to 6% CaO;
   0 to 1% SrO;
   0 to 2% refining agent;
   2 to 20 ppm $T\text{-}Fe_2O_3$ (in which $T\text{-}Fe_2O_3$ denotes a total iron oxide content obtained by converting all of iron compounds into $Fe_2O_3$); and
   0 to 200 ppm $TiO_2$.

6. The ultraviolet ray transmitting glass composition according to claim 1, wherein the content of $T\text{-}Fe_2O_3$ is 2 to 10 ppm in terms of mass ppm.

7. The ultraviolet ray transmitting glass composition according to claim 6, wherein the content of $T\text{-}Fe_2O_3$ is 2 to 6 ppm in terms of mass ppm.

8. The ultraviolet ray transmitting glass composition according to claim 1, wherein the ultraviolet ray transmitting glass composition comprises at least one component selected from the group consisting of $SO_3$, Cl, and F as the refining agent, and the contents of the components, in terms of mass %, are as follows: 0 to 1% $SO_3$; 0 to 1% Cl; and 0 to 1% F.

9. The ultraviolet ray transmitting glass composition according to claim 8, wherein the ultraviolet ray transmitting glass composition comprises $SO_3$ as the refining agent, and the content of $SO_3$ exceeds 0% but is not more than 1% in terms of mass %.

10. The ultraviolet ray transmitting glass composition according to claim 8, wherein the ultraviolet ray transmitting glass composition comprises $SO_3$ as the refining agent, and the content of $SO_3$ is 0.01 to 1% in terms of mass %.

11. The ultraviolet ray transmitting glass composition according to claim 8, wherein the ultraviolet ray transmitting glass composition comprises $SO_3$ as the refining agent, and the content of $SO_3$ is 0.1 to 0.5% in terms of mass %.

12. The ultraviolet ray transmitting glass composition according to claim 8, wherein the ultraviolet ray transmitting glass composition comprises Cl as the refining agent, and the content of Cl is 0% or more but less than 0.1% in terms of mass %.

13. The ultraviolet ray transmitting glass composition according to claim 1, wherein the ultraviolet ray transmittance is at least 70%.

14. The ultraviolet ray transmitting glass composition according to claim 13, wherein the ultraviolet ray transmittance is at least 80%.

15. The ultraviolet ray transmitting glass composition according to claim 1, wherein the content of FeO that is converted to $Fe_2O_3$ in $T\text{-}Fe_2O_3$ is at least 31%.

16. The ultraviolet ray transmitting glass composition according to claim 1, wherein the ultraviolet ray transmitting glass composition has an average linear thermal expansion coefficient in a range of 50 to 350° C. of 80 to $100 \times 10^{-7}$/° C.

17. A glass article making use of an ultraviolet ray transmitting glass composition, wherein the ultraviolet ray transmitting glass composition is an ultraviolet ray transmitting glass composition according to claim 1.

18. The glass article according to claim 17, wherein the glass article is a bioanalytical device.

* * * * *